(12) United States Patent
Moore et al.

(10) Patent No.: US 7,122,351 B2
(45) Date of Patent: Oct. 17, 2006

(54) DIMERIZED PDGF-D AND MATERIALS AND METHODS FOR PRODUCING IT

(75) Inventors: Margaret Dow Moore, Seattle, WA (US); Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 665 days.

(21) Appl. No.: 10/274,638

(22) Filed: Oct. 18, 2002

(65) Prior Publication Data

US 2003/0109000 A1    Jun. 12, 2003

Related U.S. Application Data

(60) Provisional application No. 60/346,117, filed on Oct. 19, 2001.

(51) Int. Cl.
*C12N 5/10* (2006.01)
*C12N 15/16* (2006.01)
*C12N 15/63* (2006.01)

(52) U.S. Cl. ............. 435/69.4; 435/252.3; 435/254.11; 435/320.1; 536/23.4; 536/23.5; 536/23.51

(58) Field of Classification Search ..................... None
See application file for complete search history.

(56) References Cited

U.S. PATENT DOCUMENTS

| | | | | |
|---|---|---|---|---|
| 5,013,653 | A * | 5/1991 | Huston et al. ............. 435/69.7 |
| 5,116,964 | A | 5/1992 | Capon et al. ................. 536/27 |
| 5,565,335 | A | 10/1996 | Capon et al. ............. 435/64.7 |
| 5,731,168 | A | 3/1998 | Carter et al. ............... 435/69.1 |
| 6,291,212 | B1 | 9/2001 | Sledziewski et al. ...... 435/69.1 |
| 6,403,769 | B1 | 6/2002 | Larochelle et al. ...... 530/387.3 |
| 6,495,668 | B1 | 12/2002 | Gilbert et al. ............. 530/399 |
| 6,642,356 | B1 | 11/2003 | Humphreys ................. 530/327 |
| 6,706,687 | B1 | 3/2004 | Eriksson et al. ............... 514/12 |
| 2003/0049816 | A1 | 3/2003 | Baker et al. ................. 435/183 |

FOREIGN PATENT DOCUMENTS

| | | |
|---|---|---|
| EP | 0452364 B1 | 5/2002 |
| WO | 01/40466 A2 | 6/2001 |
| WO | 01/55430 A1 | 8/2001 |
| WO | 02/02781 A1 | 1/2002 |
| WO | 02/072607 A2 | 9/2002 |

OTHER PUBLICATIONS

U.S. Appl. No. 10/365,095, filed Feb. 11, 2003, Fox et al.
Fischer et al., *Nature Biotechnology* 15:142-145, 1997.
Bergsten et al., *Nature Cell Biology* 3:512-516, 2001.
LaRochelle et al., *Nature Cell Biology* 3:517-521, 2001.

* cited by examiner

*Primary Examiner*—Prema Mertz
(74) *Attorney, Agent, or Firm*—Gary E. Parker

(57) ABSTRACT

Proteins consisting of two PDGF-D polypeptide chains, polynucleotides encoding the polypeptides, and materials and methods for making the proteins are disclosed. Each of the polypeptide chains consists of, from amino terminus to carboxyl terminus, the following operably linked segments: P1-P2-h-$C_H2$-$C_H3$; P1-P2-$C_H2$-$C_H3$; h-$C_H2$-$C_H3$-P2-P1; or $C_H2$-$C_H3$-P2-P1. Within these polypeptide chains, P1 is a first polypeptide segment as shown in SEQ ID NO:2 or SEQ ID NO:4 from amino acid x to amino acid y, wherein x is an integer from 246 to 258, inclusive, and y is an integer from 365–370, inclusive; P2 is a second polypeptide segment consisting of from 4 to 20 amino acid residues; h is an immunoglobulin hinge region or portion thereof; and $C_H2$ and $C_H3$ are $C_H2$ and $C_H3$ domains of an immunoglobulin heavy chain, respectively. Within the protein, the two polypeptide chains are joined by one or more disulfide bonds, each of the chains is optionally glycosylated, and the protein binds to and activates cell-surface PDGF receptors.

26 Claims, 3 Drawing Sheets

```
                              LC                          HC            HC
                              |                           |             |
                 218 221      |    222                    |             |   230
wt          |Glu Pro Lys Ser Cys Asp Lys Thr His Thr Cys Pro Pro Cys Pro|
Fc-488      |  .   .  Arg  .  Ser  .   .   .   .   .   .   .   .   .   . |
Fc4         |  .   .  Arg  .  Ser  .   .   .   .   .   .   .   .   .   . |
Fc5         |  .   .   .   .  Ser  .   .   .   .   .   .   .   .   .   . |
Fc6         |  .   .   .   .  Ser  .   .   .   .   .   .   .   .   .   . |
Fc7         |  .   .   .   .   .   .   .   .   .   .   .   .   .   .   . |
            |                         <- hinge ->                        |

234 235     237                               245
wt          |Ala Pro Glu Leu Leu Gly Gly Pro Ser Val Phe Leu Phe Pro Pro
Fc-488      |  .   .   .   .   .   .   .   .   .   .   .   .   .   .   .
Fc4         |  .   .   .  Ala Glu  .  Ala  .   .   .   .   .   .   .   .
Fc5         |  .   .   .  Ala Glu  .  Ala  .   .   .   .   .   .   .   .
Fc6         |  .   .   .  Ala Glu  .  Ala  .   .   .   .   .   .   .   .
Fc7         |  .   .   .   .   .   .   .   .   .   .   .   .   .   .   .
            |CH2 ->

260
wt           Lys Pro Lys Asp Thr Leu Met Ile Ser Arg Thr Pro Glu Val Thr
Fc-488        .   .   .   .   .   .   .   .   .   .   .   .   .   .   .
Fc4           .   .   .   .   .   .   .   .   .   .   .   .   .   .   .
Fc5           .   .   .   .   .   .   .   .   .   .   .   .   .   .   .
Fc6           .   .   .   .   .   .   .   .   .   .   .   .   .   .   .
Fc7           .   .   .   .   .   .   .   .   .   .   .   .   .   .   .

275
wt           Cys Val Val Val Asp Val Ser His Glu Asp Pro Glu Val Lys Phe
Fc-488        .   .   .   .   .   .   .   .   .   .   .   .   .   .   .
Fc4           .   .   .   .   .   .   .   .   .   .   .   .   .   .   .
Fc5           .   .   .   .   .   .   .   .   .   .   .   .   .   .   .
Fc6           .   .   .   .   .   .   .   .   .   .   .   .   .   .   .
Fc7           .   .   .   .   .   .   .   .   .   .   .   .   .   .   .

290
wt           Asn Trp Tyr Val Asp Gly Val Glu Val His Asn Ala Lys Thr Lys
Fc-488        .   .   .   .   .   .   .   .   .   .   .   .   .   .   .
Fc4           .   .   .   .   .   .   .   .   .   .   .   .   .   .   .
Fc5           .   .   .   .   .   .   .   .   .   .   .   .   .   .   .
Fc6           .   .   .   .   .   .   .   .   .   .   .   .   .   .   .
Fc7           .   .   .   .   .   .   .   .   .   .   .   .   .   .   .

297                                      305
wt           Pro Arg Glu Glu Gln Tyr Asn Ser Thr Tyr Arg Val Val Ser Val
Fc-488        .   .   .   .   .   .   .   .   .   .   .   .   .   .   .
Fc4           .   .   .   .   .   .   .   .   .   .   .   .   .   .   .
Fc5           .   .   .   .   .   .   .   .   .   .   .   .   .   .   .
Fc6           .   .   .   .   .   .   .   .   .   .   .   .   .   .   .
Fc7           .   .   .   .   .   .  Gln  .   .   .   .   .   .   .   .
```

*Fig. 1A*

|        |     |     |     |     |     |     |     |     |     |     |     |     |     | 320 |
|--------|-----|-----|-----|-----|-----|-----|-----|-----|-----|-----|-----|-----|-----|-----|
| wt     | Leu | Thr | Val | Leu | His | Gln | Asp | Trp | Leu | Asn | Gly | Lys | Glu | Tyr | Lys |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

|        |     |     |     |     |     |     |     |     | 330 | 331 |     |     |     | 335 |
|--------|-----|-----|-----|-----|-----|-----|-----|-----|-----|-----|-----|-----|-----|-----|
| wt     | Cys | Lys | Val | Ser | Asn | Lys | Ala | Leu | Pro | Ala | Pro | Ile | Glu | Lys | Thr |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | Ser | Ser | .   | .   | .   | .   |
| Fc5    | .   | .   | .   | .   | .   | .   | .   | .   | .   | Ser | Ser | .   | .   | .   | .   |
| Fc6    | .   | .   | .   | .   | .   | .   | .   | .   | .   | Ser | Ser | .   | .   | .   | .   |
| Fc7    | .   | .   | .   | .   | .   | .   | .   | .   | .   | .   | .   | .   | .   | .   | .   |

|        |     |     |     |     |     |     |     |     |     |     |     |     |     | 350 |
|--------|-----|-----|-----|-----|-----|-----|-----|-----|-----|-----|-----|-----|-----|-----|
| wt     | Ile | Ser | Lys | Ala | Lys | Gly | Gln | Pro | Arg | Glu | Pro | Gln | Val | Tyr | Thr |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

<- CH2 | CH3 ->

|        |     |     |     | 356 |     | 358 |     |     |     |     |     |     |     | 365 |
|--------|-----|-----|-----|-----|-----|-----|-----|-----|-----|-----|-----|-----|-----|-----|
| wt     | Leu | Pro | Pro | Ser | Arg | Asp | Glu | Leu | Thr | Lys | Asn | Gln | Val | Ser | Leu |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

|        |     |     |     |     |     |     |     |     |     |     |     |     |     | 380 |
|--------|-----|-----|-----|-----|-----|-----|-----|-----|-----|-----|-----|-----|-----|-----|
| wt     | Thr | Cys | Leu | Val | Lys | Gly | Phe | Tyr | Pro | Ser | Asp | Ile | Ala | Val | Glu |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

|        |     |     |     |     |     |     |     |     |     |     |     |     |     | 395 |
|--------|-----|-----|-----|-----|-----|-----|-----|-----|-----|-----|-----|-----|-----|-----|
| wt     | Trp | Glu | Ser | Asn | Gly | Gln | Pro | Glu | Asn | Asn | Tyr | Lys | Thr | Thr | Pro |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

*Fig. 1B*

|        |     |     |     |     |     |     |     |     |     |     |     |     |     | 410 |     |
|--------|-----|-----|-----|-----|-----|-----|-----|-----|-----|-----|-----|-----|-----|---------|-----|
| wt     | Pro | Val | Leu | Asp | Ser | Asp | Gly | Ser | Phe | Phe | Leu | Tyr | Ser | Lys | Leu |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

|        |     |     |     |     |     |     |     |     |     |     |     |     |     | 425 |
|--------|-----|-----|-----|-----|-----|-----|-----|-----|-----|-----|-----|-----|-----|---------|
| wt     | Thr | Val | Asp | Lys | Ser | Arg | Trp | Gln | Gln | Gly | Asn | Val | Phe | Ser | Cys |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

|        |     |     |     |     | 431 |     |     |     |     |     |     |     | 440 |
|--------|-----|-----|-----|-----|---------|-----|-----|-----|-----|-----|-----|-----|---------|
| wt     | Ser | Val | Met | His | Glu | Ala | Leu | His | Asn | His | Tyr | Thr | Gln | Lys | Ser |
| Fc-488 | .   | .   | .   | .   | .   | .   | .   | .   | .   | .   | .   | .   | .   | .   | .   |
| Fc4    | .   | .   | .   | .   | .   | .   | .   | .   | .   | .   | .   | .   | .   | .   | .   |
| Fc5    | .   | .   | .   | .   | .   | .   | .   | .   | .   | .   | .   | .   | .   | .   | .   |
| Fc6    | .   | .   | .   | .   | .   | .   | .   | .   | .   | .   | .   | .   | .   | .   | .   |
| Fc7    | .   | .   | .   | .   | .   | .   | .   | .   | .   | .   | .   | .   | .   | .   | .   |

|        |     |     |     |     | 446 |     |     |
|--------|-----|-----|-----|-----|---------|-----|-----|
| wt     | Leu | Ser | Leu | Ser | Pro | Gly | Lys | *** |
| Fc-488 | .   | .   | .   | .   | .   | .   | .   | .   |
| Fc4    | .   | .   | .   | .   | .   | .   | .   | .   |
| Fc5    | .   | .   | .   | .   | .   | .   | .   |     |
| Fc6    | .   | .   | .   | .   | .   | .   | *** |     |
| Fc7    | .   | .   | .   | .   | .   | .   | .   | .   |

*Fig. 1C*

SEQUENCE LISTING

```
<160> NUMBER OF SEQ ID NOS: 14

<210> SEQ ID NO 1
<211> LENGTH: 1882
<212> TYPE: DNA
<213> ORGANISM: Homo sapiens
<220> FEATURE:
<221> NAME/KEY: CDS
<222> LOCATION: (226)...(1338)

<400> SEQUENCE: 1
ccgtcaccat ttatcagctc agcaccacaa ggaagtgcgg cacccacacg cgctcggaaa      60
gttcagcatg caggaagttt ggggagagct cggcgattag cacagcgacc cgggccagcg     120
cagggcgagc gcaggcggcg agagcgcagg gcggcgcggc gtcggtcccg ggagcagaac     180
ccggcttttt cttggagcga cgctgtctct agtcgctgat cccaa atg cac cgg ctc     237
                                                    Met His Arg Leu
                                                     1 atc ttt gtc tac act cta atc tgc gca aac ttt tgc agc tgt cgg gac       285
Ile Phe Val Tyr Thr Leu Ile Cys Ala Asn Phe Cys Ser Cys Arg Asp
 5                  10                  15                  20 act tct gca acc ccg cag agc gca tcc atc aaa gct ttg cgc aac gcc       333
Thr Ser Ala Thr Pro Gln Ser Ala Ser Ile Lys Ala Leu Arg Asn Ala
                25                  30                  35 aac ctc agg cga gat gag agc aat cac ctc aca gac ttg tac cga aga       381
Asn Leu Arg Arg Asp Glu Ser Asn His Leu Thr Asp Leu Tyr Arg Arg
            40                  45                  50 gat gag acc atc cag gtg aaa gga aac ggc tac gtg cag agt cct aga       429
Asp Glu Thr Ile Gln Val Lys Gly Asn Gly Tyr Val Gln Ser Pro Arg
        55                  60                  65 ttc ccg aac agc tac ccc agg aac ctc ctc ctg aca tgg cgg ctt cac       477
Phe Pro Asn Ser Tyr Pro Arg Asn Leu Leu Leu Thr Trp Arg Leu His
    70                  75                  80 tct cag gag aat aca cgg ata cag cta gtg ttt gac aat cag ttt gga       525
Ser Gln Glu Asn Thr Arg Ile Gln Leu Val Phe Asp Asn Gln Phe Gly
85                  90                  95                 100 tta gag gaa gca gaa aat gat atc tgt agg tat gat ttt gtg gaa gtt       573
Leu Glu Glu Ala Glu Asn Asp Ile Cys Arg Tyr Asp Phe Val Glu Val
                105                 110                 115 gaa gat ata tcc gaa acc agt acc att att aga gga cga tgg tgt gga       621
```

|  |  |
|---|---:|
| Glu Asp Ile Ser Glu Thr Ser Thr Ile Ile Arg Gly Arg Trp Cys Gly<br>            120                    125                    130 |  |
| cac aag gaa gtt cct cca agg ata aaa tca aga acg aac caa att aaa<br>His Lys Glu Val Pro Pro Arg Ile Lys Ser Arg Thr Asn Gln Ile Lys<br>            135                    140                    145 | 669 |
| atc aca ttc aag tcc gat gac tac ttt gtg gct aaa cct gga ttc aag<br>Ile Thr Phe Lys Ser Asp Asp Tyr Phe Val Ala Lys Pro Gly Phe Lys<br>    150                    155                    160 | 717 |
| att tat tat tct ttg ctg gaa gat ttc caa ccc gca gca gct tca gag<br>Ile Tyr Tyr Ser Leu Leu Glu Asp Phe Gln Pro Ala Ala Ala Ser Glu<br>165                    170                    175                    180 | 765 |
| acc aac tgg gaa tct gtc aca agc tct att tca ggg gta tcc tat aac<br>Thr Asn Trp Glu Ser Val Thr Ser Ser Ile Ser Gly Val Ser Tyr Asn<br>                  185                    190                    195 | 813 |
| tct cca tca gta acg gat ccc act ctg att gcg gat gct ctg gac aaa<br>Ser Pro Ser Val Thr Asp Pro Thr Leu Ile Ala Asp Ala Leu Asp Lys<br>                200                    205                    210 | 861 |
| aaa att gca gaa ttt gat aca gtg gaa gat ctg ctc aag tac ttc aat<br>Lys Ile Ala Glu Phe Asp Thr Val Glu Asp Leu Leu Lys Tyr Phe Asn<br>        215                    220                    225 | 909 |
| cca gag tca tgg caa gaa gat ctt gag aat atg tat ctg gac acc cct<br>Pro Glu Ser Trp Gln Glu Asp Leu Glu Asn Met Tyr Leu Asp Thr Pro<br>230                    235                    240 | 957 |
| cgg tat cga ggc agg tca tac cat gac cgg aag tca aaa gtt gac ctg<br>Arg Tyr Arg Gly Arg Ser Tyr His Asp Arg Lys Ser Lys Val Asp Leu<br>245                    250                    255                  260 | 1005 |
| gat agg ctc aat gat gat gcc aag cgt tac agt tgc act ccc agg aat<br>Asp Arg Leu Asn Asp Asp Ala Lys Arg Tyr Ser Cys Thr Pro Arg Asn<br>                265                    270                    275 | 1053 |
| tac tcg gtc aat ata aga gaa gag ctg aag ttg gcc aat gtg gtc ttc<br>Tyr Ser Val Asn Ile Arg Glu Glu Leu Lys Leu Ala Asn Val Val Phe<br>            280                    285                    290 | 1101 |
| ttt cca cgt tgc ctc ctc gtg cag cgc tgt gga gga aat tgt ggc tgt<br>Phe Pro Arg Cys Leu Leu Val Gln Arg Cys Gly Gly Asn Cys Gly Cys<br>        295                    300                    305 | 1149 |
| gga act gtc aac tgg agg tcc tgc aca tgc aat tca ggg aaa acc gtg<br>Gly Thr Val Asn Trp Arg Ser Cys Thr Cys Asn Ser Gly Lys Thr Val<br>310                    315                    320 | 1197 |
| aaa aag tat cat gag gta tta cag ttt gag cct ggc cac atc aag agg<br>Lys Lys Tyr His Glu Val Leu Gln Phe Glu Pro Gly His Ile Lys Arg<br>325                    330                    335                  340 | 1245 |
| agg ggt aga gct aag acc atg gct cta gtt gac atc cag ttg gat cac<br>Arg Gly Arg Ala Lys Thr Met Ala Leu Val Asp Ile Gln Leu Asp His<br>                345                    350                    355 | 1293 |
| cat gaa cga tgc gat tgt atc tgc agc tca aga cca cct cga taa<br>His Glu Arg Cys Asp Cys Ile Cys Ser Ser Arg Pro Pro Arg  *<br>            360                    365                    370 | 1338 |
| gagaatgtgc acatccttac attaagcctg aaagaacctt tagtttaagg agggtgagat | 1398 |
| aagagaccct tttcctacca gcaaccaaac ttactactag cctgcaatgc aatgaacaca | 1458 |
| agtggttgct gagtctcagc cttgctttgt taatgccatg gcaagtagaa aggtatatca | 1518 |
| tcaacttcta tacctaagaa tataggattg catttaataa tagtgtttga ggttatatat | 1578 |
| gcacaaacac acacagaaat atattcatgt ctatgtgtat atagatcaaa tgttttttt | 1638 |
| ttttggtata tataaccagg tacaccagag gttacatatg tttgagttag actcttaaaa | 1698 |
| tcctttgcca aaataaggga tggtcaaata tatgaaacat gtctttagaa aatttaggag | 1758 |
| ataaatttat ttttaaattt tgaaacacga aacaattttg aatcttgctc tcttaaagaa | 1818 |
| agcatcttgt atattaaaaa tcaaaagatg aggctttctt acatatacat cttagttgat | 1878 |

```
tatt                                                                    1882

<210> SEQ ID NO 2
<211> LENGTH: 370
<212> TYPE: PRT
<213> ORGANISM: Homo sapiens

<400> SEQUENCE: 2

Met His Arg Leu Ile Phe Val Tyr Thr Leu Ile Cys Ala Asn Phe Cys
 1               5                  10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365
```

-continued

```
Pro Arg
    370

<210> SEQ ID NO 3
<211> LENGTH: 1472
<212> TYPE: DNA
<213> ORGANISM: Mus musculus
<220> FEATURE:
<221> NAME/KEY: CDS
<222> LOCATION: (93)...(1205)

<400> SEQUENCE: 3
agggactgtg cagtagaaat ccgccgactc aacccttttgg gctttattta tttacttttg          60
gagcaacgcg atccctaggt cgctgagccc aa atg caa cgg ctc gtt tta gtc          113
                                    Met Gln Arg Leu Val Leu Val
                                     1               5 tcc att ctc ctg tgc gcg aac ttt agc tgc tat ccg gac act ttt gcg          161
Ser Ile Leu Leu Cys Ala Asn Phe Ser Cys Tyr Pro Asp Thr Phe Ala
         10                  15                  20 act ccg cag aga gca tcc atc aaa gct ttg cgc aat gcc aac ctc agg          209
Thr Pro Gln Arg Ala Ser Ile Lys Ala Leu Arg Asn Ala Asn Leu Arg
 25                  30                  35 aga gat gag agc aat cac ctc aca gac ttg tac cag aga gag gag aac          257
Arg Asp Glu Ser Asn His Leu Thr Asp Leu Tyr Gln Arg Glu Glu Asn
 40                  45                  50                  55 att cag gtg aca agc aat ggc cat gtg cag agt cct cgc ttc ccg aac          305
Ile Gln Val Thr Ser Asn Gly His Val Gln Ser Pro Arg Phe Pro Asn
             60                  65                  70 agc tac cca agg aac ctg ctt ctg aca tgg tgg ctc cgt tcc cag gag          353
Ser Tyr Pro Arg Asn Leu Leu Leu Thr Trp Trp Leu Arg Ser Gln Glu
     75                  80                  85 aaa aca cgg ata caa ctg tcc ttt gac cat caa ttc gga cta gag gaa          401
Lys Thr Arg Ile Gln Leu Ser Phe Asp His Gln Phe Gly Leu Glu Glu
 90                  95                 100 gca gaa aat gac att tgt agg tat gac ttt gtg gaa gtt gaa gaa gtc          449
Ala Glu Asn Asp Ile Cys Arg Tyr Asp Phe Val Glu Val Glu Glu Val
105                 110                 115 tca gag agc agc act gtt gtc aga gga aga tgg tgt ggc cac aag gag          497
Ser Glu Ser Ser Thr Val Val Arg Gly Arg Trp Cys Gly His Lys Glu
120                 125                 130                 135 atc cct cca agg ata acg tca aga aca aac cag att aaa atc aca ttt          545
Ile Pro Pro Arg Ile Thr Ser Arg Thr Asn Gln Ile Lys Ile Thr Phe
             140                 145                 150 aag tct gat gac tac ttt gtg gca aaa cct gga ttc aag att tat tat          593
Lys Ser Asp Asp Tyr Phe Val Ala Lys Pro Gly Phe Lys Ile Tyr Tyr
         155                 160                 165 tca ttt gtg gaa gat ttc caa ccg gaa gca gcc tca gag acc aac tgg          641
Ser Phe Val Glu Asp Phe Gln Pro Glu Ala Ala Ser Glu Thr Asn Trp
     170                 175                 180 gaa tca gtc aca agc tct ttc tct ggg gtg tcc tat cac tct cca tca          689
Glu Ser Val Thr Ser Ser Phe Ser Gly Val Ser Tyr His Ser Pro Ser
 185                 190                 195 ata acg gac ccc act ctc act gct gat gcc ctg gac aaa act gtc gca          737
Ile Thr Asp Pro Thr Leu Thr Ala Asp Ala Leu Asp Lys Thr Val Ala
200                 205                 210                 215 gaa ttc gat acc gtg gaa gat cta ctt aag cac ttc aat cca gtg tct          785
Glu Phe Asp Thr Val Glu Asp Leu Leu Lys His Phe Asn Pro Val Ser
             220                 225                 230 tgg caa gat gat ctg gag aat ttg tat ctg gac acc cct cat tat aga          833
Trp Gln Asp Asp Leu Glu Asn Leu Tyr Leu Asp Thr Pro His Tyr Arg
```

```
                      235                 240                 245
ggc agg tca tac cat gat cgg aag tcc aaa gtg gac ctg gac agg ctc        881
Gly Arg Ser Tyr His Asp Arg Lys Ser Lys Val Asp Leu Asp Arg Leu
        250                 255                 260 aat gat gat gtc aag cgt tac agt tgc act ccc agg aat cac tct gtg        929
Asn Asp Asp Val Lys Arg Tyr Ser Cys Thr Pro Arg Asn His Ser Val
265                 270                 275 aac ctc agg gag gag ctg aag ctg acc aat gca gtc ttc ttc cca cga        977
Asn Leu Arg Glu Glu Leu Lys Leu Thr Asn Ala Val Phe Phe Pro Arg
280                 285                 290                 295 tgc ctc ctc gtg cag cgc tgt ggt ggc aac tgt ggt tgc gga act gtc       1025
Cys Leu Leu Val Gln Arg Cys Gly Gly Asn Cys Gly Cys Gly Thr Val
                300                 305                 310 aac tgg aag tcc tgc aca tgc agc tca ggg aag aca gtg aag aag tat       1073
Asn Trp Lys Ser Cys Thr Cys Ser Ser Gly Lys Thr Val Lys Lys Tyr
            315                 320                 325 cat gag gta ttg aag ttt gag cct gga cat ttc aag aga agg ggc aaa       1121
His Glu Val Leu Lys Phe Glu Pro Gly His Phe Lys Arg Arg Gly Lys
        330                 335                 340 gct aag aat atg gct ctt gtt gat atc cag ctg gat cat cat gag cga       1169
Ala Lys Asn Met Ala Leu Val Asp Ile Gln Leu Asp His His Glu Arg
345                 350                 355 tgt gac tgt atc tgc agc tca aga cca cct cga taa aacactatgc            1215
Cys Asp Cys Ile Cys Ser Ser Arg Pro Pro Arg  *
360                 365                 370 acatctgtac tttgattatg aaaggacctt taggttacaa aaaccctaag aagcttctaa     1275
tctcagtgca atgaatgcat atggaaatgt tgctttgtta gtgccatggc aagaagaagc     1335
aaatatcatt aatttctata tacataaaca taggaattca cttatcaata gtatgtgaag     1395
atatgtatat atacttatat acatgactag ctctatgtat gtaaatagat taaatacttt     1455
attcagtata tttactg                                                     1472

<210> SEQ ID NO 4
<211> LENGTH: 370
<212> TYPE: PRT
<213> ORGANISM: Mus musculus

<400> SEQUENCE: 4

Met Gln Arg Leu Val Leu Val Ser Ile Leu Leu Cys Ala Asn Phe Ser
1               5                   10                  15

Cys Tyr Pro Asp Thr Phe Ala Thr Pro Gln Arg Ala Ser Ile Lys Ala
            20                  25                  30

Leu Arg Asn Ala Asn Leu Arg Arg Asp Glu Ser Asn His Leu Thr Asp
        35                  40                  45

Leu Tyr Gln Arg Glu Glu Asn Ile Gln Val Thr Ser Asn Gly His Val
    50                  55                  60

Gln Ser Pro Arg Phe Pro Asn Ser Tyr Pro Arg Asn Leu Leu Leu Thr
65                  70                  75                  80

Trp Trp Leu Arg Ser Gln Glu Lys Thr Arg Ile Gln Leu Ser Phe Asp
                85                  90                  95

His Gln Phe Gly Leu Glu Glu Ala Glu Asn Asp Ile Cys Arg Tyr Asp
            100                 105                 110

Phe Val Glu Val Glu Glu Val Ser Glu Ser Ser Thr Val Val Arg Gly
        115                 120                 125

Arg Trp Cys Gly His Lys Glu Ile Pro Pro Arg Ile Thr Ser Arg Thr
    130                 135                 140

Asn Gln Ile Lys Ile Thr Phe Lys Ser Asp Asp Tyr Phe Val Ala Lys
```

```
                145                 150                 155                 160
Pro Gly Phe Lys Ile Tyr Tyr Ser Phe Val Glu Asp Phe Gln Pro Glu
                    165                 170                 175
Ala Ala Ser Glu Thr Asn Trp Glu Ser Val Thr Ser Ser Phe Ser Gly
                180                 185                 190
Val Ser Tyr His Ser Pro Ser Ile Thr Asp Pro Thr Leu Thr Ala Asp
            195                 200                 205
Ala Leu Asp Lys Thr Val Ala Glu Phe Asp Thr Val Glu Asp Leu Leu
        210                 215                 220
Lys His Phe Asn Pro Val Ser Trp Gln Asp Asp Leu Glu Asn Leu Tyr
225                 230                 235                 240
Leu Asp Thr Pro His Tyr Arg Gly Arg Ser Tyr His Asp Arg Lys Ser
                245                 250                 255
Lys Val Asp Leu Asp Arg Leu Asn Asp Asp Val Lys Arg Tyr Ser Cys
                260                 265                 270
Thr Pro Arg Asn His Ser Val Asn Leu Arg Glu Glu Leu Lys Leu Thr
                275                 280                 285
Asn Ala Val Phe Phe Pro Arg Cys Leu Leu Val Gln Arg Cys Gly Gly
290                 295                 300
Asn Cys Gly Cys Gly Thr Val Asn Trp Lys Ser Cys Thr Cys Ser Ser
305                 310                 315                 320
Gly Lys Thr Val Lys Lys Tyr His Glu Val Leu Lys Phe Glu Pro Gly
                325                 330                 335
His Phe Lys Arg Arg Gly Lys Ala Lys Asn Met Ala Leu Val Asp Ile
                340                 345                 350
Gln Leu Asp His His Glu Arg Cys Asp Cys Ile Cys Ser Ser Arg Pro
                355                 360                 365
Pro Arg
    370

<210> SEQ ID NO 5
<211> LENGTH: 232
<212> TYPE: PRT
<213> ORGANISM: Homo sapiens
<220> FEATURE:
<221> NAME/KEY: VARIANT
<222> LOCATION: (3)...(3)
<223> OTHER INFORMATION: Xaa = Lys or Arg
<220> FEATURE:
<221> NAME/KEY: VARIANT
<222> LOCATION: (5)...(5)
<223> OTHER INFORMATION: Xaa = Cys or Ser
<220> FEATURE:
<221> NAME/KEY: VARIANT
<222> LOCATION: (19)...(19)
<223> OTHER INFORMATION: Xaa = Leu or Ala
<220> FEATURE:
<221> NAME/KEY: VARIANT
<222> LOCATION: (20)...(20)
<223> OTHER INFORMATION: Xaa = Leu or Glu
<220> FEATURE:
<221> NAME/KEY: VARIANT
<222> LOCATION: (22)...(22)
<223> OTHER INFORMATION: Xaa = Gly or Ala
<220> FEATURE:
<221> NAME/KEY: VARIANT
<222> LOCATION: (82)...(82)
<223> OTHER INFORMATION: Xaa = Asn or Gln
<220> FEATURE:
<221> NAME/KEY: VARIANT
<222> LOCATION: (115)...(115)
<223> OTHER INFORMATION: Xaa = Ala or Ser
<220> FEATURE:
<221> NAME/KEY: VARIANT
```

```
<222> LOCATION: (116)...(116)
<223> OTHER INFORMATION: Xaa = Pro or Ser
<220> FEATURE:
<221> NAME/KEY: VARIANT
<222> LOCATION: (232)...(232)
<223> OTHER INFORMATION: Xaa = Lys or not present

<400> SEQUENCE: 5
```

| | | | | | | | | | | | | | | |
|---|---|---|---|---|---|---|---|---|---|---|---|---|---|---|
|Glu|Pro|Xaa|Ser|Xaa|Asp|Lys|Thr|His|Thr|Cys|Pro|Pro|Cys|Pro|Ala|
|1| | |5| | | | |10| | | | |15| |

| | | | | | | | | | | | | | | |
|---|---|---|---|---|---|---|---|---|---|---|---|---|---|---|
|Pro|Glu|Xaa|Xaa|Gly|Xaa|Pro|Ser|Val|Phe|Leu|Phe|Pro|Pro|Lys|Pro|
| | |20| | | |25| | | |30| | | | |

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Xaa Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Xaa Xaa Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Xaa
225                 230

```
<210> SEQ ID NO 6
<211> LENGTH: 5
<212> TYPE: PRT
<213> ORGANISM: Artificial Sequence
<220> FEATURE:
<223> OTHER INFORMATION: polypeptide, linker peptide

<400> SEQUENCE: 6

Ser Gly Ser Gly Ser
1               5

<210> SEQ ID NO 7
<211> LENGTH: 5
<212> TYPE: PRT
<213> ORGANISM: Artificial Sequence
<220> FEATURE:
<223> OTHER INFORMATION: polypeptide, enterokinase cleavage site

<400> SEQUENCE: 7

Asp Asp Asp Asp Lys
1               5
```

```
<210> SEQ ID NO 8
<211> LENGTH: 4
<212> TYPE: PRT
<213> ORGANISM: Artificial Sequence
<220> FEATURE:
<223> OTHER INFORMATION: polypeptide, factor Xa cleavage site

<400> SEQUENCE: 8

Ile Glu Gly Arg
 1

<210> SEQ ID NO 9
<211> LENGTH: 8
<212> TYPE: PRT
<213> ORGANISM: Artificial Sequence
<220> FEATURE:
<223> OTHER INFORMATION: polypeptide, rhinovirus 3C protease cleavage
      site

<400> SEQUENCE: 9

Leu Glu Val Leu Phe Gln Gly Pro
 1               5

<210> SEQ ID NO 10
<211> LENGTH: 4
<212> TYPE: PRT
<213> ORGANISM: Artificial Sequence
<220> FEATURE:
<223> OTHER INFORMATION: polypeptide, furin cleavage site
<220> FEATURE:
<221> NAME/KEY: VARIANT
<222> LOCATION: (2)...(2)
<223> OTHER INFORMATION: Xaa = Any Amino Acid
<220> FEATURE:
<221> NAME/KEY: VARIANT
<222> LOCATION: (3)...(3)
<223> OTHER INFORMATION: Xaa = Lys or Arg

<400> SEQUENCE: 10

Arg Xaa Xaa Arg
 1

<210> SEQ ID NO 11
<211> LENGTH: 48
<212> TYPE: DNA
<213> ORGANISM: Artificial Sequence
<220> FEATURE:
<223> OTHER INFORMATION: oligonucleotide primer ZC38,515

<400> SEQUENCE: 11
atgcatagat cttgatcctg atcctgatcg aggtggtctt gagctgca                48

<210> SEQ ID NO 12
<211> LENGTH: 36
<212> TYPE: DNA
<213> ORGANISM: Artificial Sequence
<220> FEATURE:
<223> OTHER INFORMATION: oligonucleotide primer ZC29,007

<400> SEQUENCE: 12
atgcattccg gatcatacca tgaccggaag tcaaaa                              36

<210> SEQ ID NO 13
<211> LENGTH: 17
<212> TYPE: DNA
<213> ORGANISM: Artificial Sequence
<220> FEATURE:
```

-continued

```
<223> OTHER INFORMATION: oligonucleotide primer ZC447

<400> SEQUENCE: 13
taacaatttc acacagg                                                  17

<210> SEQ ID NO 14
<211> LENGTH: 18
<212> TYPE: DNA
<213> ORGANISM: Artificial Sequence
<220> FEATURE:
<223> OTHER INFORMATION: oligonucleotide primer ZC976

<400> SEQUENCE: 14
cgttgtaaaa cgacggcc                                                 18
```

DIMERIZED PDGF-D AND MATERIALS AND METHODS FOR PRODUCING IT

CROSS-REFERENCE TO RELATED APPLICATION

This application claims the benefit under 35 U.S.C. 119(e) of provisional application No. 60/346,117, filed Oct. 19, 2001.

BACKGROUND OF THE INVENTION

PDGF-D is a recently discovered member of the platelet-derived growth factor (PDGF) family (Bergsten et al., *Nature Cell Biol.* 3:512–516, 2001; LaRochelle et al., *Nature Cell Biol.* 3:517–521, 2001). PDGF-D is also referred to as "zvegf4" (WIPO Publication WO 00/66736).

The PDGF-D polypeptide has a multidomain structure that comprises an amino-terminal CUB domain and a carboxyl-terminal growth factor domain joined by an interdomain region of approximately 70 amino acid residues. The growth factor domain of PDGF-D, which comprises approximately residues 250–370 of SEQ ID NO:2, is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295–307, 1991; Soker et al., *Cell* 92:735–745, 1998), human bone morphogenetic protein-1 (Wozney et al., *Science* 242:1528–1534, 1988), porcine seminal plasma protein and bovine acidic seminal fluid protein (Romero et al., *Nat. Struct. Biol.* 4:783–788, 1997), and *Xenopus laevis* tolloid-like protein (Lin et al., *Dev. Growth Differ.* 39:43–51, 1997).

PDGF-D forms a homodimeric protein (PDGF-DD) that is proteolytically cleaved to produce the active species, a growth factor domain dimer. The active protein binds to and activates the β/β and α/β isoforms of the PDGF receptor on the cell surface. PDGF-DD dimers are mitogenic for a variety of mesenchymal cells (Bergsten et al. ibid.; LaRochelle et al., ibid.). In addition, PDGF-D has been shown to have bone-forming activity in mice (WIPO publication WO 01/57083).

DESCRIPTION OF THE INVENTION

Within one aspect of the present invention there is provided a protein consisting of two polypeptide chains, each of the polypeptide chains consisting of, from amino terminus to carboxyl terminus, the following operably linked segments: P1-P2-h-$C_H2$-$C_H3$, P1-P2-$C_H2$-$C_H3$, h-$C_H2$-$C_H3$-P2-P1, or $C_H2$-$C_H3$-P2-P1. Within these polypeptide chains, P1 is a first polypeptide segment as shown in SEQ ID NO:2 or SEQ ID NO:4 from amino acid x to amino acid y, wherein x is an integer from 246 to 258, inclusive, and y is an integer from 365–370, inclusive; P2 is a second polypeptide segment consisting of from 4 to 20 amino acid residues; h is an immunoglobulin hinge region or portion thereof; and $C_H2$ and $C_H3$ are $C_H2$ and $C_H3$ domains of an immunoglobulin heavy chain, respectively. Within the protein, the two polypeptide chains are joined by one or more disulfide bonds, each of the chains is optionally glycosylated, and the protein binds to and activates cell-surface PDGF receptors. Within one embodiment, y is 370. Within other embodiments, x is 246, 248, or 250. Within another embodiment, x is 250 and y is 370. Within further embodiments, the second polypeptide segment consists of from 5 to 15 amino acid residues. Within an additional embodiment, the second polypeptide segment consists of 10 amino acid residues. Within still other embodiments, the second polypeptide segment consists of glycine and serine residues. Within related embodiments, the second polypeptide segment is [Ser-Gly-Ser-Gly-Ser]$_x$, wherein x is 1 or 2. Within further embodiments, the second polypeptide segment does not contain Lys or Arg, the second polypeptide segment does not contain Cys, or the second polypeptide segment does not contain Pro. Within other embodiments, the second polypeptide segment comprises a proteolytic cleavage site, such as a plasmin cleavage site, a thrombin cleavage site, or a factor Xa cleavage site. Within still further embodiments, each of the two polypeptide chains consists of P1-P2-h-$C_H2$-$C_H3$, wherein h-$C_H2$-$C_H3$ consists of a sequence of amino acid residues as shown in SEQ ID NO:5.

Within a second aspect of the invention there is provided a polynucleotide encoding a polypeptide fusion consisting of, from amino terminus to carboxyl terminus, the following operably linked segments: P1-P2-h-$C_H2$-$C_H3$, P1-P2-$C_H2$-$C_H3$, h-$C_H2$-$C_H3$-P2-P1, or $C_H2$-$C_H3$-P2-P1, wherein P1, P2, h, $C_H2$, and $C_H3$ are as defined above. Within one embodiment, the polynucleotide further encodes a secretory peptide operably linked to the polypeptide fusion. Within another embodiment, the polynucleotide is DNA.

Within a third aspect of the invention there is provided an expression vector comprising the following operably linked elements: a transcription promoter; a DNA polynucleotide as disclosed above; and a transcription terminator.

Within a fourth aspect of the invention there is provided a cultured cell into which has been introduced an expression vector as disclosed above. Within one embodiment, the second polypeptide segment comprises a proteolytic cleavage site and the cell produces a protease that cleaves at the cleavage site.

Within a fifth aspect of the invention there is provided a method of making a protein comprising the steps of culturing a cell as disclosed above in a culture medium whereby the DNA polynucleotide is expressed and the polypeptide fusion is produced, and recovering the polypeptide fusion. Within one embodiment, the cell is a eukaryotic cell, the DNA polynucleotide futher encodes a secretory peptide operably linked to the polypeptide fusion, and the polypeptide fusion is secreted from the cell as a disulfide-bonded dimer and is recovered from the culture medium. Within another embodiment, the second polypeptide segment comprises a proteolytic cleavage site and, subsequent to the recovering step, the polypeptide fusion is proteolytically cleaved at the cleavage site. Within a further embodiment, the second polypeptide segment comprises a proteolytic cleavage site, the cell produces a protease that cleaves at the cleavage site, the polypeptide fusion is produced and cleaved by the protease within the cell to produce a plurality of cleavage products, and at least one of the cleavage products of the polypeptide fusion is recovered.

Within a sixth aspect of the invention there is provided a protein produced by one of the methods disclosed above.

These and other aspects of the invention are illustrated by the following detailed description and the attached drawing.

The drawing (FIGS. 1A–1C) illustrates the amino acid sequences of certain immunoglobulin Fc polypeptides (SEQ ID NO:5). Amino acid sequence numbers are based on the EU index (Kabat et al., *Sequences of Proteins of Immunological Interest*, US Department of Health and Human Services, NIH, Bethesda, 1991). The illustrated sequences include a wild-type human sequence ("wt") and five variant sequences, designated Fc-488, Fc4, Fc5, Fc6, and Fc7. The Cys residues normally involved in disulfide bonding to the light chain constant region (LC) and heavy chain constant region (HC) are indicated. A "." indicates identity to wild-type at that position. *** indicates the amino terminus; the C-terminal Lys residue has been removed from Fc6. Boundaries of the hinge, $C_H2$, and $C_H3$ domains are shown.

As used herein, the phrase "a cultured cell into which has been introduced an expression vector" includes cells that have been physically manipulated to contain the vector, as well as progeny of the manipulated cells when the progeny also contain the vector.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

An immunoglobulin "Fc" fragment (or Fc domain) is the portion of an antibody which is responsible for binding to antibody receptors on cells and the C1q component of complement. Fe stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, $C_H2$, and $C_H3$ domains. However, the term has more recently been applied to a single chain consisting of $C_H3$, $C_H2$, and at least a portion of the hinge sufficient to form a disulfide-linked dimer with a second such chain. For a complete review of immunoglobulin structure and function see Putnam, *The Plasma Proteins*, Vol V, Academic Press, Inc., 49–140, 1987; and Padlan, *Mol. Immunol.* 31:169–217, 1994. As used herein, the term Fc also includes certain variants of naturally occuring sequences as disclosed in more detail below.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated polynucleotide molecules of the present invention are free of other genes with which they are ordinarily associated, but may include naturally occurring 5' and 3' untranslated regions such as promoters and terminators. The identification of associated regions will be evident to one of ordinary skill in the art (see, for example, Dynan and Tijan, *Nature* 316:774–778, 1985).

An "isolated" polypeptide or protein is a polypeptide or protein that is found in a condition other than its native environment, such as apart from blood and animal tissue. Within one embodiment, the isolated polypeptide or protein is substantially free of other polypeptides or proteins, particularly other polypeptides or proteins of animal origin. Isolated polypeptides or proteins may be provided in a highly purified form, i.e., greater than 95% pure or greater than 99% pure. When used in this context, the term "isolated" does not exclude the presence of the same polypeptide or protein in alternative physical forms, such as dimers or alternatively glycosylated or derivatized forms.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

The term "PDGF-D polypeptide" is used herein to denote a polypeptide comprising the core growth factor domain of a PDGF-D (e.g., residues 258–365 of human PDGF-D (SEQ ID NO:2) or mouse PDGF-D (SEQ ID NO:4)). A PDGF-D polypeptide may further comprise one or more additional amino acids derived from the full-length PDGF-D polypeptide chain or from a heterologous polypeptide. Using methods known in the art, PDGF-D polypeptides can be prepared in a variety of forms, including glycosylated or non-glycosylated, pegylated or non-pegylated, with or without an initial methionine residue, and as fusion polypeptides. PDGF-D polypeptides may be in the form of monomers or disulfide-bonded dimers.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

A representative human PDGF-D polypeptide sequence (primary translation product) is shown in SEQ ID NO:2, and a representative mouse PDGF-D polypeptide sequence is shown in SEQ ID NO:4. DNAs encoding these polypeptides are shown in SEQ ID NOS:1 and 3, respectively. Those skilled in the art will recognize that these sequences represent single alleles of the respective human and mouse genes, and that allelic variation is expected to exist. Analysis of the amino acid sequence shown in SEQ ID NO:2 indicates that residues 1 to 18 form a secretory peptide. The primary translation product also includes a CUB domain extending from approximately residue 52 to approximately residue 179; a propeptide-like sequence extending from approximately residue 180 to either residue 245, residue 249, or residue 257 with four potential cleavage sites, including monobasic sites at residue 245 and residue 249, a dibasic site at residues 254–255, and a target site for furin or a furin-like protease at residues 254–257; and the carboxyl-terminal growth factor domain disclosed above. Protein produced by expressing the full-length DNA in a baculovirus expression system showed cleavage between residues 249 and 250, as well as longer species with amino termini at residues 19 and 35. Cleavage of full-length PDGF-DD dimer with plasmin resulted in activation of the protein. By Western analysis, a band migrating at approximately the same size as the growth factor domain was observed. A matched, uncleaved, full-length PDGF-DD sample demonstrated no activity.

While not wishing to be bound by theory, it is believed that the PDGF-D growth factor domain forms anti-parallel dimers, as do the PDGF A and B polypeptides. It is also believed that the two PDGF-D polypeptides within a dimer are joined by at least one interchain disulfide bond.

The present invention provides materials and methods for enhanced production of PDGF-D growth factor domain dimers. Expression of full-length PDGF-D and the isolated growth factor domain in a baculovirus system has been found to result in low levels of biologically active protein. Increasing selective pressure did not produce satisfactory expression levels. When a truncated PDGF-D polypeptide beginning at Arg-250 of SEQ ID NO:2 was produced in cultured insect and mammalian cells, a substantial portion of the secreted product was in an inactive, monomeric form. Thus, the present inventors sought means to increase production of biologically active PDGF-DD proteins.

Within the present invention, disulfide-bonded dimers of PDGF-D polypeptides are produced by expressing, in a cultured host cell, a polynucleotide encoding a fused polypeptide chain consisting of a first polypeptide which is a PDGF-D growth factor domain polypeptide, a second polypeptide which is a linker polypeptide, and a third polypeptide which is an immunoglobulin (Ig) heavy chain fragment, wherein the second polypeptide is positioned between the first and third polypeptides and joined to them by peptide bonds. Within one embodiment of the invention the three polypeptides are joined, from amino terminus to carboxyl terminus, as first polypeptide—second polypeptide—third polypeptide. Within another embodiment of the invention the three polypeptides are joined, from amino terminus to carboxyl terminus, as third polypeptide—second polypeptide—first polypeptide. Depending upon the type of host cell, the PDGF-D polypeptide is produced as a monomer or as a dimer. If the PDGF-D polypeptide is produced as a monomer, it can be recovered and dimerized according to routine methods as disclosed in more detail below.

The PDGF-D growth factor domain polypeptide consists of a sequence of amino acid residues as shown in SEQ ID NO:2 or SEQ ID NO:4 from amino acid x to amino acid y, wherein x is an integer from 246 to 258, inclusive, and y is an integer from 365–370, inclusive. Thus, the PDGF-D growth factor domain polypeptide may consist of, for example, residues 246–370 of SEQ ID NO:2, residues 247–370 of SEQ ID NO:2, residues 248–370 of SEQ ID NO:2, residues 249–370 of SEQ ID NO:2, residues 250–370 of SEQ ID NO:2, residues 251–370 of SEQ ID NO:2, residues 252–370 of SEQ ID NO:2, residues 253–370 of SEQ ID NO:2, residues 254–370 of SEQ ID NO:2, residues 255–370 of SEQ ID NO:2, residues 256–370 of SEQ ID NO:2, residues 257–370 of SEQ ID NO:2, or residues 258–370 of SEQ ID NO:2. Within other embodiments of the invention the PDGF-D growth factor domain polypeptide has an amino-terminus of one of the polypeptides disclosed above, and a carboxyl terminus at residue 365 of SEQ ID NO:2, residue 366 of SEQ ID NO:2, residue 367 of SEQ ID NO:2, residue 368 of SEQ ID NO:2, residue 369 of SEQ ID NO:2, or residue 370 of SEQ ID NO:2. Within other embodiments the PDGF-D growth factor domain polypeptide consists of the corresponding residues of SEQ ID NO:4.

The second (linker) polypeptide is designed to provide, within the dimerized, fused polypeptide chains, a distance of approximately 40 Å between the carboxyl termini of the two PDGF-D growth factor domain polypeptides. Required linker lengths can be determined through molecular modeling by predicting the distance between the termini of the Ig heavy chain components of the fusion protein. For example, the distance between the amino termini of the component chains of an Fc fragment is predicted to be approximately 24 Å, hence each linker polypeptide should span at least 8 Å and will preferably span more than 8 Å to more readily accommodate the three-dimensional structure of the molecule. Calculation of the effective length of a polypeptide in solution is routine in the art. See, for example, Creighton, *Proteins: Structures and Molecular Properties,* $2^{nd}$ edition, W. H. Freeman and Company, 1993, Chapter 5. In general, the linker polypeptide consists of at least 4 amino acid residues and may be as long as 20 residues.

The linker polypeptide should have an overall hydrophilic character and be non-immunogenic and flexible. As used herein, a "flexible" linker is one that lacks a substantially stable higher-order conformation in solution. Areas of local charge are to be avoided. In general, small, polar, and hydrophilic residues are preferred, and bulky and hydrophobic residues are undesirable. If the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Cys, Pro, Leu, Ile, Lys, and Arg residues will be avoided, Cys residues due to their potential for formation of unwanted disulfide bonds, Pro residues due to their hydrophobicity and lack of flexibility, and Lys and Arg residues due to potential immunogenicity. However, these less desirable residues may be included to provide a specific proteolytic cleavage site as disclosed below. Exemplary linkers are those having the structure [Ser-Gly-Ser-Gly-Ser]$_x$ (SEQ ID NO:6), wherein x is 1 or 2. Within certain embodiments of the invention the linker polypeptide comprises a proteolytic cleavage site to facilitate separation of the Ig heavy chain fragments from the dimerized PDGF-D growth factor domain polypeptides. Exemplary proteolytic cleavage sites include sequences cleaved by plasmin, thrombin, factor Xa, enterokinase, furin, and rhinovirus 3C protease. The use of these and other proteases to cleave fusion proteins is known in the art. See, for example, Rubinstein et al., WO 00/61768; van de Ven et al., U.S. Pat. No. 5,935,815; and Fischer et al., U.S. Pat. No. 6,010,844. Thrombin cleaves after the dipeptide sequence Arg-Pro. Enterokinase cleaves after the pentapeptide sequence Asp-Asp-Asp-Asp-Lys (SEQ ID NO:7). Factor Xa cleaves after the sequence Ile-Glu-Gly-Arg (SEQ ID NO:8). Plasmin cleaves after the sequence Arg-Pro. The human rhinovirus 3C protease cleaves Gln-Gly peptide bonds, such as in the sequence Leu-Glu-Val-Leu-Phe-Gln-Gly-Pro (SEQ ID NO:9). Furin cleaves after Arg-Xaa-Lys/Arg-Arg (SEQ ID NO:10).

The third polypeptide segment comprises the $C_H2$ and $C_H3$ domains of an immunoglobulin heavy chain. The third polypeptide segment may further comprise a hinge region or portion thereof. The hinge region or portion thereof provides additional spacing between the first and third polypeptides and, if the hinge region contains one or more Cys residues, can contribute to stabilization of the dimeric protein through disulfide bond formation. Thus, within certain embodiments of the invention the third polypeptide segment consists of hinge, $C_H2$, and $C_H3$ (i.e., an Fc fragment chain). Within other embodiments the hinge region is modified to remove the cysteine residue than forms a disulfide bond with the light chain, such as by truncation of the hinge or by amino acid substitution as shown in FIGS. 1A–1C. Five classes of immunoglobulin, or antibody, protein (IgG, IgA, IgM, IgD, and IgE) have been identified in higher vertebrates. IgG comprises the major class as it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. DNA sequences encoding human immunoglobulin chains are known in the art. See, for example, Ellison et al., *Nucleic Acids Res.* 10:4071–4079, 1982; Kenten et al., *Proc. Natl. Acad. Sci. USA* 79:6661–6665, 1982; Seno et al., Nuc. Acids Res. 11:719–726, 1983; and GenBank Accession No. J00228. The γ hinge region is preferred for use within the present invention.

Fusion of an immunoglobulin polypeptide to a PDGF-D polypeptide may extend the in vivo half-life of a PDGF-DD dimer. IgG1 sequences are particularly useful in this regard since IgG1 has the longest serum half-life of any of the serum proteins (average $t_{1/2}$=21–24 days).

Certain amino acid subsititutions may be introduced into the immunoglobulin portion to alter effector functions and other properties associated with the native Ig constant region domains. Several of the specific amino acid residues that are important for antibody constant region-mediated activity in the IgG1 subclass have been identified (Burton and Woof, *Adv. Immunol.* 51:1–84, 1992; Sarmay et al., *Mol Immunol.* 5:633–639, 1992; Kim et al., *Eur J Immunol.* 24:542–548, 1994; Morgan et al., *Immunology* 2:319–324, 1995; and Ghetie et al., *Nature Biotechnol.* 15:637–40, 1997). Inclusion or exclusion of these specific amino acid residues allows for inclusion or exclusion of specific Ig constant region-mediated activity. Modified Ig sequences can be used within the present invention to build fusion proteins with specified activity defined by the particular Ig sequence used. For example, amino acid substitutions can be made at EU index positions 234, 235, and 237 to reduce binding to Fc γ receptor-1 (FcγRI), and at EU index positions 330 and 331 to reduce complement fixation. See, Duncan et al., *Nature* 332:563–564, 1988; Winter et al., U.S. Pat. No. 5,624,821; Tao et al., *J. Exp. Med.* 178:661, 1993; and Canfield and Morrison, *J. Exp. Med.* 173:1483, 1991. The carboxyl-terminal lysine residue can be removed from the $C_H3$ domain to increase homogeneity of the product. The Cys residue within the hinge region that is ordinarily disulfide-bonded to the light chain (EU index position 222) can be replaced with another amino acid residue, such as a serine residue. Exemplary sequences are shown in FIGS. 1A–1C (SEQ ID NO:5).

As noted above, the first polypeptide may be positioned at either the amino terminus or the carboxyl terminus of the fusion polypeptide. The present invention thus comprises four classes of fusion polypeptides as follows:

$$n\text{-}P1\text{-}P2\text{-}h\text{-}C_H2\text{-}C_H3\text{-}c \quad (I)$$

$$n\text{-}P1\text{-}P2\text{-}C_H2\text{-}C_H3\text{-}c \quad (II)$$

$$n\text{-}h\text{-}C_H2\text{-}C_H3\text{-}P2\text{-}P_1\text{-}c \quad (III)$$

$$n\text{-}C_H2\text{-}C_H3\text{-}P2\text{-}P1\text{-}c \quad (IV)$$

wherein n is the amino terminus, c is the carboxyl terminus, P1 is the first (PDGF-D growth factor domain) polypeptide, P2 is the second (linker) polypeptide, h is an immunoglobulin hinge region, and $C_H2$ and $C_H3$ are $C_H2$ and $C_H3$ domains of an immunoglobulin heavy chain, respectively. Within each class, the linker polypeptide may be designed to provide the optimum spacing between the first and second polypeptides. For polypeptides of class I, the linker will preferably provide a spacing of from 8 to 13 Å. Thus, linkers in class I polypeptides will ordinarily not exceed 13 amino acid residues in length and will more commonly consist of from 4 to 8 amino acid residues. For polypeptides of class II, the linker will preferably provide a spacing of from 14 to 19 Å. Thus, linkers in class II polypeptides will ordinarily not exceed 19 residues in length and will more commonly consist of from 5 to 12 residues. Within polypeptides of class m and class IV, the linker will preferably provide a spacing of from 11 to 16 Å. Thus, linkers in class III and class tV polypeptides will ordinarily not exceed 16 residues in length and will more commonly consist of from 4 to 10 residues. However, those skilled in the art will recognize that a certain amount of flexibility exists in the design of linker polypeptides. The present invention thus includes, without limitation, the use of linker polypeptides of 4, 5, 6, 7, 8, 9, 10, 11, 12, 13, 14, 15, 16, 17, 18, 19, and 20 residues within each of fusion polypeptide classes I through IV.

The present invention also provides polynucleotide molecules, including DNA and RNA molecules, that encode the PDGF-D polypeptides disclosed above. The polynucleotides of the present invention include both single-stranded and double-stranded molecules. A representative DNA sequence encoding human PDGF-D is set forth in SEQ ID NO:1, and a representative DNA sequence encoding mouse PDGF-D is set forth in SEQ ID NO:3. Additional DNA sequences encoding PDGF-D polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding PDGF-D polypeptides.

Methods for preparing DNA and RNA are well known in the art. Complementary DNA (cDNA) clones are prepared from RNA that is isolated from a tissue or cell that produces large amounts of PDGF-D RNA. Such tissues and cells are identified by Northern blotting (Thomas, *Proc. Natl. Acad. Sci. USA* 77:5201, 1980), and include heart, pancreas, stomach, and adrenal gland. Total RNA can be prepared using guanidine HCl extraction followed by isolation by centrifugation in a CsCl gradient (Chirgwin et al., *Biochemistry* 18:52–94, 1979). Poly (A)$^+$ RNA is prepared from total RNA using the method of Aviv and Leder (*Proc. Natl. Acad. Sci. USA* 69:1408–1412, 1972). Complementary DNA is prepared from poly(A)$^+$ RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequences disclosed herein, or parts thereof, for probing or priming a library. Polynucleotides encoding PDGF-D polypeptides are identified and isolated by, for example, hybridization or polymerase chain reaction ("PCR", Mullis, U.S. Pat. No. 4,683,202). Expression libraries can be probed with antibodies to PDGF-D, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See, in general, Glick and Pasternak, *Molecular Biotechnology, Principles & Applications of Recombinant DNA*, ASM Press, Washington, D.C., 1994; Itakura et al., *Ann. Rev. Biochem.* 53: 323–356, 1984; and Climie et al., *Proc. Natl. Acad. Sci. USA* 87:633–637, 1990.

The PDGF-D polypeptides of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual*, 2$^{nd}$ ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a PDGF-D polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a PDGF-D polypeptide into the secretory pathway of a host cell, a secretory signal sequence (also known as a leader sequence, prepro sequence or pre sequence) is provided in the expression vector. The secretory signal sequence may be that of a PDGF-D, or may be derived from another secreted protein (e.g., t-PA; see, U.S. Pat. No. 5,641,655) or synthesized de novo. The secretory signal sequence is operably linked to the PDGF-D DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of PDGF-D polypeptides via a host cell secretory pathway is expected to result in the production of dimeric proteins. Dimers may also be assembled in vitro upon incubation of component polypeptides under suitable conditions. In general, in vitro assembly will include incubating the protein mixture under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Manassas, Va. Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, 10801 University Blvd., Manassas, Va. USA under accession numbers 98669 and 98668, respectively, and derivatives of these vectors.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, Chapman & Hall, London; O'Reilly et al., *Baculovirus Expression Vectors: A Laboratory Manual*, Oxford University Press., New York, 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566–4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. In addition, transfer vectors can include an in-frame fusion with DNA encoding a polypeptide extension or affinity tag as disclosed above. Using techniques known in the art, a transfer vector containing a PDGF-D polypeptide-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses PDGF-D protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See, in general, Glick and Pasternak, ibid. See also, U.S. Pat. No. 5,300,435. Serum-free media are used to grow and maintain the cells. Suitable media formulations are known in the art and can be obtained from commercial suppliers. The cells are grown up from an inoculation density of approximately $2-5 \times 10^5$ cells to a density of $1-2 \times 10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii*, and *Candida maltosa* are known in the art. See, for example, Gleeson et al., *J. Gen. Microbiol.* 132:3459–3465, 1986; Cregg, U.S. Pat. No. 4,882,279; and Raymond et al., *Yeast* 14:11–23, 1998. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli*, *Bacillus* and other genera are also useful host cells within the present invention. Techniques for transforming these hosts and expressing foreign DNA sequences cloned therein are well known in the art (see, e.g., Sambrook et al., ibid.). When expressing a PDGF-D polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

When the second polypeptide segment comprises a proteolytic cleavage site, the PDGF-D polypeptides can be cleaved within the host cell to remove the third polypeptide (Ig portion) if the host cell produces a protease that cleaves at the cleavage site. If the host cell does not naturally produce the protease, it can be transfected to co-express the protease and the PDGF-D polypeptide. See, for example, U.S. Pat. Nos. 5,648,254 and 5,935,815.

Proteins of the present invention that contain a cleavage site in the second polypeptide can also be cleaved in vitro according to conventional methods. The use of proteases for processing recombinant proteins is routine in the art and includes the use of immobilized proteases. See, for example, U.S. Pat. No. 6,010,844. Specific reaction conditions are based on the protease to be used and will be adjusted to minimize unwanted proteolysis with the first polypeptide segment. In general, such parameters as reaction time and ratio of protease to substrate will be adjusted to obtain the desired result.

Proteins of the present invention are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising an immunoglobulin heavy chain polypeptide can be purified by affinity chromatography on immobilized protein A. Additional purification steps, such as gel filtration, can be used to obtain the desired level of purity or to provide for desalting, buffer exchange, and the like.

PDGF-DD proteins can be used wherever it is desired to stimulate the production of bone and/or connective tissue in both humans and non-human animals. Veterinary uses include use in domestic animals, including livestock and companion animals. Specific applications include, without limitation, fractures, including non-union fractures and fractures in patients with compromised healing, such as diabetics, alcoholics, and the aged; bone grafts; healing bone following radiation-induced osteonecrosis; implants, including joint replacements and dental implants; repair of bony defects arising from surgery, such as cranio-maxilofacial repair following tumor removal, surgical reconstruction following tramatic injury, repair of hereditary or other physical abnormalities, and promotion of bone healing in plastic surgery; treatment of periodontal disease and repair of other dental defects; treatment of bone defects following therapeutic treatment of bone cancers; increase in bone formation during distraction osteogenesis; treatment of joint injuries, including repair of cartilage and ligament; repair of joints that have been afflicted with osteoarthritis; tendon repair and re-attachment; treatment of osteoporosis (including age-related osteoporosis, post-menopausal osteoporosis, glutocorticoid-induced osteoporosis, and disuse osteoporosis) and other conditions characterized by increased bone loss or decreased bone formation; elevation of peak bone mass in pre-menopausal women; and use in the healing of connective tissues associated with dura mater.

For pharmaceutical use, PDGF-DD proteins are formulated for local or systemic (particularly intravenous or subcutaneous) delivery according to conventional methods. In general, pharmaceutical formulations will include a PDGF-DD protein in combination with a pharmaceutically acceptable delivery vehicle. Delivery vehicles include biocompatible solid or semi-solid matrices, including powdered bone, ceramics, biodegradable and non-biodegradable synthetic polymers, and natural polymers; tissue adhesives (e.g., fibrin-based); aqueous polymeric gels; aqueous solutions; liposomes; and the like. These and other suitable vehicles are known in the art. Formulations may further include one or more additional growth factors, excipients, preservatives, solubilizers, buffering agents, albumin to prevent protein loss on vial surfaces, etc. Methods of formulation are well known in the art and are disclosed, for example, in *Remington: The Science and Practice of Pharmacy*, 20th ed., Gennaro et al., eds., Lippincott, Williams & Wilkins, Baltimore, 2000. An "effective amount" of a composition is that amount that produces a statistically significant effect, such as a statistically significant increase in the rate of fracture repair, reversal of bone loss in osteoporosis, increase in the rate of healing of a joint injury, increase in the reversal of cartilage defects, increase or acceleration of bone growth into prosthetic devices, improved repair of dental defects, and the like. The exact dose will be determined by the clinician according to accepted standards, taking into account the nature and severity of the condition to be treated, patient traits, etc. Determination of dose is within the level of ordinary skill in the art. Depending upon the route and method of administration, the protein may be administered in a single dose, as a prolonged infusion, or intermittently over an extended period. Intravenous administration will be by bolus injection or infusion over a typical period of one to several hours. Sustained release formulations can be employed. In general, a therapeutically effective amount of a PDGF-DD protein is an amount sufficient to produce a clinically significant change in the treated condition, such as a clinically significant reduction in time required for fracture repair, a significant reduction in the volume of a void or other defect, a significant increase in bone density, a significant reduction in morbidity, or a significantly increased histological score.

PDGF-DD will ordinarily be used in a concentration of about 10 to 100 µg/ml of total volume, although concentrations in the range of 1 ng/ml to 1000 µg/ml may be used. For local application, such as for the regeneration of bone in a fracture or other bony defect, the protein will be applied in the range of 0.1–100 µg/cm$^2$ of wound area.

PDGF-DD can be used in combination with other growth factors and other therapeutic agents that have a positive effect on the growth of bone or connective tissue. Such growth factors include insulin-like growth factor 1 (IGF-1), other PDGFs, alpha and beta transforming growth factors (TGF-α and TGF-β), epidermal growth factor (EGF), bone morphogenetic proteins, leukemia inhibitory factor, and fibroblast growth factors. Other therapeutic agents include vitamin D, bisphosphonates, calcitonin, estrogens, parathyroid hormone, osteogenin, NaF, osteoprotegerin, and statins.

The invention is further illustrated by the following, non-limiting examples.

EXAMPLE 1

An insect cell expression vector, designated pZBV37L: GFD(zVEGF4)FLX1Fc4, was designed to express a PDGF-D growth factor domain polypeptide with a downstream 5 amino acid flexible linker sequence (SEQ ID NO:6), followed by two amino acid residues coded for by the presence of a BglII site, and a C-terminal Fc4 fragment. The sequence of the Fc4 fragment is shown in FIGS. 1A–1C (SEQ ID NO:5, wherein residue 3 is Arg, residue 5 is Ser, residue 19 is Ala, residue 20 is Glu, residue 22 is Ala, residue 82 is Asn, residue 115 is Ser, residue 119 is Ser, and residue 232 is Lys). Fc4 was produced by PCR cloning from a human fetal liver cDNA library followed by several rounds of PCR amplification to introduce the sequence changes shown in FIGS. 1A–1C.

A 401-bp fragment (designated GFD(zVEGF4)Flx1) containing BspEI and BglII restriction sites on the 5' and 3' ends, respectively, was generated by PCR amplification from a plasmid containing PDGF-D cDNA using primers ZC38,515 (SEQ ID NO:11) and ZC29,007 (SEQ ID NO:12). A 100-µl PCR reaction mixture was prepared using commercially available reagents (EXPAND High Fidelity PCR System; Boehringer Mannheim, Indianapolis, Ind.). The reaction mixture was incubated at 94° C. for 2 minutes; then 35 cycles of 94° C. for 15 seconds, 50° C. for 30 seconds, and 72° C. for 60 seconds; a 5-minute incubation at 72° C.; followed by 4° C. soak. Five µl of the reaction mixture was visualized by electrophoresis on a 1% agarose gel. The remainder of the reaction mixture was purified using a commercially available PCR purification kit (obtained from Qiagen, Inc., Valencia, Calif.) according to the manufacturer's instructions and eluted in 30 µl water. The recovered cDNA (PCR product) was digested in a 35 µl volume using BspEI and BglII (New England Biolabs, Beverly, Mass.) in appropriate buffer conditions for 1 hour at 37° C. The digested PCR product band was run through a 1% agarose TAE gel, excised, extracted using a spin column containing a silica gel membrane (QIAQUICK Gel Extraction Kit; Qiagen, Inc.), and eluted in 30 µl of water. The digested GFD(zVEGF4)Flx1 PCR product and a previously prepared Fc4 fragment cDNA with BglII and XbaI ends were ligated into the multiple cloning site (MCS) of vector pZBV37L in a 3-way ligation. The pZBV37L vector was prepared from the PFASTBAC1 expression vector (Life Technologies, Gaithersburg, Md.) by replacing the polyhedron promoter with the late activating Basic Protein Promoter and the EGT leader signal sequence upstream of the multiple cloning site (MCS). Five µl of the restriction-digested GFD(zVEGF4) Flx1, 5 µl of the prepared Fc4 fragment, and approximately 50 ng of the pZBV37L vector were ligated overnight at 16° C. in a 20 µl volume. Three µl of the ligation mixture was transformed into 30 µl of E. coli host cells (ELECTROMAX DH12S; Life Technologies) by electroporation at 400 Ohms, 2V, and 25 µF in a 2-mm gap electroporation cuvette (BTX, Model No. 620). The transformed cells were diluted in 350 µl of SOC media (2% BACTO Tryptone (Difco Laboratories, Detroit, Mich.), 0.5% BACTO Yeast Extract (Difco Laboratories), 10 ml 1 M NaCl, 1.5 mM KCl, 10 mM MgCl$_2$, 10 mM MgSO$_4$, and 20 mM glucose) and grown for 1 hour at 37° C., then 50 µl of the dilution was plated onto LB plates containing 100 µg/ml ampicillin. Clones were analyzed by PCR, and positive clones were selected, plated, and sequenced. Once proper sequence was confirmed, 25 ng of positive clone DNA was transformed into 100 µl competent E. coli cells (MAX EFFICIENCY DH10BAC Competent Cells; Life Technologies) by heat shock for 45 seconds in a 42° C. heat block. The transformed cells were diluted in 900 µl SOC media and outgrown at 37° C. for 1 hour, then 100 µl was plated onto Luria Agar plates containing 50 µg/ml kanamycin, 7 µg/ml gentamicin, 10 µg/ml tetracycline, 40 µg/mL IPTG, and 200 µg/mL halogenated indolyl-β-D-galactoside (bluo-gal). The plates were incubated for 48 hours at 37° C. A color selection was used to identify those cells having transposed viral DNA (referred to as a "bacmid"). White colonies were analyzed by PCR, and positive colonies (containing the desired bacmid) were selected for outgrowth and purified. Clones were screened for the correct molecular weight insert by amplifying DNA using primers to the transposable element in the bacmid (ZC447, SEQ ID NO:13; ZC976, SEQ ID NO:14). The PCR reaction conditions were 1 cycle at 94° C. for 2 minutes; 25 cycles of 94° C. for 10 seconds, 50° C. for 30 seconds, and 72° C. for 120 seconds; 1 cycle at 72° C. for 5 min; followed by a 4° C. soak. The PCR product was run on a 1% agarose gel to check the insert size.

Clones having the correct size insert (as determined by PCR) were used to transfect Spodoptera frugiperda (Sf9) cells after culture outgrowth and bacmid isolation. Sf9 cells were seeded at 1×10$^6$ cells per well in a 6-well plate and allowed to attach for 1 hour at 27° C. Approximately five µg of bacmid DNA was diluted with 100 µl of a commercially available, protein-free insect cell culture medium (Sf-900 II SFM; Life Technologies). Twenty µl of a 3:1 (w/w) liposome formulation of the polycationic lipid 2,3-dioleyloxy-N-[2 (sperminecarboxamido)ethyl]-N,N-dimethyl-1-propaniminium-trifluoroacetate and the neutral lipid dioleoyl phosphatidylethanolamine in membrane-filtered water (LIPOFECTAMINE Reagent; Life Technologies) was diluted with 100 µl Sf-900 II SFM. The bacmid DNA and lipid solutions were gently mixed and incubated for 45 minutes at room temperature. Eight hundred microliters of Sf-900 II SFM was added to the lipid-DNA mixture. The media was aspirated from the well, and the 1 ml of DNA-lipid mix was added to the cells. The cells were incubated at 27° C. overnight. The DNA-lipid mix was aspirated off, and 2 ml of Sf-900 II media was added to each plate. The plates were incubated at 27° C., 90% humidity, for approximately 7 days, after which the virus was harvested.

Sf9 cells were seeded at 1×10$^6$ cells per well in a 6-well plate in 2 ml SF-900II. 500 µl of virus from the transfection plate was placed in the well, and the plate was incubated at 27° C., 90% humidity for 96 hours, after which the virus was harvested (primary amplification). A second round of amplification was carried out under the same conditions using 100

µl of virus from the primary amplification plate. For a third round of amplification, Sf9 cells were grown in 50 ml Sf-900 II SFM in a 250-ml shake flask to an approximate density of $1 \times 10^6$ cells/ml. They were then infected with 500 µl of the viral stock from the second-round plate and incubated at 27° C. for 3 days, after which time the virus was harvested.

The viral stock was titered by a growth inhibition curve, and the titer culture that indicated a MOI of 1 was allowed to proceed for a total of 48 hours. The supernatant was analyzed via a non-reduced Western blot using a primary monoclonal antibody specific for the growth factor domain of PDGF-D (antibody E3595) and a HRP-conjugated goat anti-mouse secondary antibody. Results indicated a dimer band with an apparent molecular weight of approximately 79 kDa and additional, higher molecular weight species. Supernatant was also provided for activity analysis.

A large viral stock was then generated. Sf9 cells were grown in IL Sf-900 II SFM in a 2800-ml shake flask to an approximate density of $1 \times 10^6$ cells/ml. They were then infected with 10 ml of the viral stock from the $3^{rd}$ round amplification and incubated at 27° C. for 96 hours, after which time the virus was harvested.

Larger scale infections were completed to provide material for downstream purification.

EXAMPLE 2

An expression vector, designated pZBV37L:GFD (zVEGF4)FLX2Fc4, was designed to express a PDGF-D growth factor domain polypeptide with a downstream 10 amino acid flexible linker sequence (two copies of SEQ ID NO:6), followed by two amino acid residues coded for by the presence of a BglII site, and a C-terminal Fc4 fragment. The vector was constructed essentially as disclosed in Example 1 using a 416-bp fragment (designated GFD (zVEGF4)Flx2) containing BspE I and Bgl II restriction sites on the 5' and 3' ends, respectively, that was generated by PCR amplification from the PCR fragment GFD (zVEGF4)Flx1 disclosed in Example 1.

Sf9 cells were transfected and viral stocks generated as disclosed in Example 1. Larger scale infections were completed to provide material for downstream purification.

EXAMPLE 3

Recombinant PDGF-D/Fc4 fusion proteins were produced from baculovirus-infected Sf9 cells as disclosed in Examples 1 and 2. Approximately two liters of conditioned media each was harvested and filtered through NALGENE 0.21 µm filters.

Proteins were purified from the filtered media by a combination of protein A affinity chromatography and gel exclusion chromatography. The filtered culture media were directly loaded onto a 20×57 mm (18-ml bed volume) protein A affinity column (POROS 50; PerSeptive Biosystems, Framingham, Mass.) at a flow of about 20 ml/minute. Following column washing for ten column volumes of 5×PBS, bound protein was eluted by five column volumes of 0.1 M glycine, pH 3.0 at 10 ml/minute. Fractions of 1.5 ml each were collected into tubes containing 50 µl of 2.0 M Tris, pH 8.0, in order to neutralize the eluted proteins. Samples from the affinity column were analyzed by SDS-PAGE with Coomassie staining and Western blotting for the presence of the PDGF-D/Fc4 fusion proteins using a rabbit anti-human IgG(Fc) antibody conjugated to horseradish peroxidase (HRP). Protein-containing fractions were pooled and concentrated to about 10 ml using a membrane filter (BIOMAX-30 concentrator; Millipore Corp., Bedford, Mass.) and loaded onto a 20×170 mm gel filtration column (SEPHADEX G-25 Fine; Amersham Pharmacia Biotech, Piscataway, N.J.) in 1×PBS, pH 7.3. The fractions containing purified protein were pooled, filtered through a 0.2 µm filter, aliquoted into 100 or 200 µl each, and frozen at −80° C. The concentrations of the final purified proteins were determined by BCA assay (Pierce Chemical Co., Rockford, Ill.) and amino acid analysis.

The recombinant proteins were analyzed by SDS-PAGE (NOVEX NUPAGE 4–12% gel; Invitrogen, Carlsbad, Calif.) with Coomassie staining and Western blotting using rabbit anti-human IgG(Fc)-HRP. Conditioned media or purified protein was electrophoresed using a commercially available blotting apparatus (NOVEX XCELL II mini-cell; Invitrogen) and transferred to nitrocellulose (0.2 µm; Bio-Rad Laboratories, Hercules, Calif.) at room temperature using blotting apparatus with stirring according to directions provided in the instrument manual. The transfer was run at 500 mA for one hour in a buffer containing 25 mM Tris base, 200 mM glycine, and 20% methanol. The filters were then blocked with 10% non-fat dry milk in PBS for 10 minutes at room temperature. The nitrocellulose was quickly rinsed, then the antibody (1:2000) was added in PBS containing 2.5% non-fat dry milk. The blots were incubated for two hours at room temperature, or overnight at 4° C., with gentle shaking. Following the incubation, the blots were washed three times for 10 minutes each in PBS, then quickly rinsed in $H_2O$. The blots were developed using commercially available chemiluminescent substrate reagents (SUPERSIGNAL ULTRA reagents 1 and 2 mixed 1:1; reagents obtained from Pierce Chemical Co.), and the signal was captured using commercially available software (LUMI-IMAGER LumiAnalyst 3.0; Boehringer Mannheim GmbH, Germany) for exposure times ranging from 10 seconds to 5 minutes or as necessary.

The purified proteins appeared as single bands with either the Coomassie or silver staining with apparent molecular weights of about 100 kDa under non-reducing conditions and about 50 kDa under reducing conditions, indicating a dimeric form under non-reducing conditions as expected.

EXAMPLE 4

PDGF-D-Fc4 fusion proteins produced by baculovirus-infected cells were tested for biological activity using an assay designed to detect activation of cell-surface PDGF receptors. Rat stellate cells were grown in 96-well tissue clusters (FALCON; BD, Franklin Lakes, N.J.) in DMEM (Life Technologies) supplemented with 10% fetal bovine serum (Hyclone Laboratories, Inc., Logan, Utah). The next day, the medium was switched to serum-free medium by substituting 0.1% BSA (Fraction V, Sigma, St. Louis, Mo.) for serum. This medium also contained the adenoviral construct KZ136, which encodes a luciferase reporter minigene driven by SRE and STAT elements, at a 1000:1 multiplicity of infection (m.o.i.). After allowing 24 hours for the incorporation of the adenoviral construct into the cells, the media were changed and replaced with serum-free media +0.1% BSA that contained purified recombinant proteins or conditioned media from insect cells at the indicated final concentration. Four hours later the cells were lysed, and luciferase activity, indicating activation of the reporter gene, was determined in the lysate using a commercially available assay kit (obtained from Promega Corp., Madison, Wis.) and a luminescence reader (MICROLUMAT PLUS, Berthold Technologies, Bad Wildbad, Germany). Results were obtained as relative luciferase units (RLU) in the lysate.

The quality of the purified proteins was analysed by SDS-PAGE, silver staining, and western blotting. All purified proteins ran at the expected size for their respective dimer forms; the apparent molecular weight for GFD-(Linker)1-Fc4 (comprising a 5-residue linker peptide) and GFD-(Linker)2-Fc4 (comprising a 10-residue linker peptide) was ~75 kDa under non-reducing conditions.

Bioactivity of these purified proteins and of a PDGF-D GFD dimer is shown below, expressed as RLU in stellate cell lysates:

| ng/ml | GFD dimer | GFD-(Linker)1-Fc4 | GFD-(Linker)2-Fc4 |
|---|---|---|---|
| 0.3 | 160 | 160 | 160 |
| 1 | 278 | 160 | 182 |

-continued

| ng/ml | GFD dimer | GFD-(Linker)1-Fc4 | GFD-(Linker)2-Fc4 |
|---|---|---|---|
| 3 | 400 | 157 | 197 |
| 10 | 542 | 150 | 171 |
| 30 | 672 | 170 | 259 |
| 100 | 826 | 276 | 290 |
| 300 | 883 | 440 | 444 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A polynucleotide encoding a polypeptide fusion consisting of, from amino terminus to carboxyl terminus, the following operably linked segments:

P1-P2-h-$C_H2$-$C_H3$;

P1-P2-$C_H2$-$C_H3$;

h-$C_H2$-$C_H3$-P2-P1; or $C_H2$-$C_H3$-P2-P1;

wherein:
P1 is a first polypeptide segment as shown in SEQ ID NO:2 or SEQ ID NO:4 from amino acid x to amino acid y, wherein x is an integer from 246 to 258, inclusive, and y is an integer from 365 to 370, inclusive;
P2 is a second polypeptide segment consisting of from 4 to 20 amino acid residues;
h is an immunoglobulin hinge region or portion thereof; and $C_H2$ and $C_H3$ are $C_H2$ and $C_H3$ domains of an immunoglobulin heavy chain, respectively.

2. The polynucleotide of claim 1 wherein the polynucleotide further encodes a secretory peptide operably linked to the polypeptide fusion.

3. The polynucleotide of claim 1 which is DNA.

4. An expression vector comprising the following operably linked elements:
a transcription promoter;
a polynucleotide according to claim 3; and
a transcription terminator.

5. A cultured cell into which has been introduced the expression vector of claim 4.

6. The cell of claim 5 wherein the second polypeptide segment comprises a proteolytic cleavage site and the cell produces a protease that cleaves at said cleavage site.

7. A method of making a protein comprising the steps of:
culturing the cell of claim 5 in a culture medium whereby the polynucleotide is expressed and the polypeptide fusion is produced; and
recovering the polypeptide fusion.

8. The method of claim 7 wherein the cell is a eukaryotic cell, the polynucleotide further encodes a secretory peptide operably linked to the polypeptide fusion, and the polypeptide fusion is secreted from the cell as a disulfide-bonded dimer and is recovered from the culture medium.

9. The method of claim 7 wherein the second polypeptide segment comprises a proteolytic cleavage site and, subsequent to the recovering step, the polypeptide fusion is proteolytically cleaved at the cleavage site.

10. A method of making a protein comprising the steps of:
culturing the cell of claim 6 in a culture medium whereby the polynucleotide is expressed and the polypeptide fusion is produced and cleaved by the protease within the cell to produce a plurality of cleavage products; and
recovering at least one of the cleavage products of the polypeptide fusion.

11. The polynucleotide of claim 1 wherein P2 is a hydrophilic polypeptide that lacks a substantially stable higher-order conformation in solution.

12. The polynucleotide of claim 1 wherein y is 370.

13. The polynucleotide of claim 1 wherein x is 246, 248, or 250.

14. The polynucleotide of claim 1 wherein x is 250 and y is 370.

15. The polynucleotide of claim 1 wherein P2 consists of from 5 to 15 amino acid residues.

16. The polynucleotide of claim 1 wherein P2 consists of 10 amino acid residues.

17. The polynucleotide of claim 1 wherein P2 consists of glycine and serine residues.

18. The polynucleotide of claim 1 wherein P2 is [Ser-Gly-Ser-Gly-Ser]$_x$, wherein x is 1 or 2.

19. The polynucleotide of claim 1 wherein P2 does not contain Lys or Arg.

20. The polynucleotide of claim 1 wherein P2 does not contain Cys.

21. The polynucleotide of claim 1 wherein P2 does not contain Pro.

22. The polynucleotide of claim 1 wherein P2 comprises a proteolytic cleavage site.

23. The polynucleotide of claim 22 wherein the cleavage site is a plasmin cleavage site, a thrombin cleavage site, or a factor Xa cleavage site.

24. The polynucleotide of claim 1 wherein h comprises a cysteine residue.

25. The polynucleotide of claim 1 wherein each of the two polypeptide chains consists of P1-P2-h-$C_H2$-$C_H3$ and wherein h-$C_H2$-$C_H3$ consists of a sequence of amino acid residues as shown in SEQ ID NO:5.

26. The polynucleotide of claim 25 wherein, within SEQ ID NO:5, residue 3 is Arg, residue 5 is Ser, residue 19 is Ala, residue 20 is Glu, residue 22 is Ala, residue 82 is Asn, residue 115 is Ser, residue 119 is Ser, and residue 232 is Lys.

* * * * *